US00PP08664P

United States Patent [19]

Desclaux

[11] Patent Number: Plant 8,664

[45] Date of Patent: Mar. 29, 1994

[54] STANDARD CARNATION NAMED SOLAR

[75] Inventor: Jean-Louis Desclaux, Angers, France

[73] Assignee: Laboratorie de Physiologie Vegetale, Le Pradet, France

[21] Appl. No.: 971,406

[22] Filed: Nov. 4, 1992

[51] Int. Cl.[5] ..... A01H 5/00
[52] U.S. Cl. ..... Plt./70.1
[58] Field of Search ..... Plt. 70.1

*Primary Examiner*—Howard J. Locker
*Assistant Examiner*—Bruce R. Campell
*Attorney, Agent, or Firm*—Tilton, Fallon, Lungmus & Chestnut

[57] ABSTRACT

A new and distinctive standard carnation cultivar particularly distinguished by its profuse production of large size flowers having a serrated edge. The outer petals are carrot red with delft rose and dresden yellow stripes and a greenish base, the flowers being carried on strong and upright stems.

1 Drawing Sheet

BACKGROUND OF THE NEW PLANT

This standard carnation cultivar originated as a hybrid seedling produced at Le Pradet, France by my crossing of two plants, hereinafter identified, selected from a field of various carnation varieties maintained at the nursery for breeding purposes. This particular seedling was selected from those produced by the said crossing because of the very unusual flower coloration on a plant having abundant foliage and favorable growth characteristics. This carnation has been asexually reproduced at our nursery in San Remo, Italy. Lonbira (U.S. Pat. No. 5,513) is the most similar commercially available cultivar. Solar differs from Lonbira in its bigger flowers, its more serrated petal and its thicker stem. Under my direction, propagation was done by means of cuttings. The initial success of the propagation was coninued through several successive generations which proved that the new variety retained all of the distinguished characteristics and that these characteristics hold true from generation to generation and appear to be firmly fixed.

DESCRIPTION OF THE DRAWINGS

My new carnation cultivar is illustrated by the accompanying photographic drawing which, in full color, shows the form and coloration of the flowers as they appear. The colors shown are as nearly true to these herein specified as is reasonably possible to obtain by conventional photographic procedures.

DESCRIPTION OF THE NEW PLANT

The following is a detailed description of my new carnation plant as observed from plants grown under greenhouse conditions in Le Pradet, France, with the stated flower colors being according to the R.H.S. Colour Chart of The Royal Horticultural Society of London, England.

THE PLANT

Origin: Seedling.

Parentage:

*Seed parent.*—Plant number B555P. B555P is a pink colored standard carnation that is about 8 centimeters in diameter, contains a serrated petal and has a stem length greater than 60 cm. B555P has never been commercialized.

*Pollen parent.* Plant number S112V. S112V is a purple colored, yellow striped standard carnation that is about 8 centimeters in diameter, has a very serrated petal and a stem length about 60 centimeters. S112V has never been commercialized.

These parent plants are so identified in my business records of the present cultivar maintained at the office of the San Remo nursery and the production of the aforementioned hybrid and the selected seedling are also there recorded.

Classification: *Dianthus caryophyllus* L.

*Commercial.*—Carnation.

Form: A strong erect bush having at least four stems emitted near the ground.

Height: About 96 cm. (at 8 months).

Cane length: Less than 15 cm owing to pinching.

Branching character: The plant is made up of to 5 main branches in average, which are prolonged by a vertical inflorescence, and which have in the lower part shoots that themselves are productive of flowers.

Growth: Vigorous, upright with rigid strength producing 0 to 6 flowers per plant per month.

Foliage:

*Quantity.*—Abundant.

*Number of leaves.*—More than 120.

*Size and shape of leaf.*—The leaf is 10.6×0.9 cm at the 7th node and oblong in shape.

*Margin type.*—Recurved.

*Texture.*—Leathery.

*Color.*—Upper side — RHS 137A. Under side — RHS 137A.

*Ribs and veins.*—Hardly noticeable.

*Rachis.*—Hardly noticeable.

THE BUD

Size:

*Shape.*—Globular.

*Diameter.*—2.7 cm.

*Length.*—2.7 cm.

*Color of petals.*—Color of base of the petal: RHS 145-D. Color of the petals when the sepals first divide: RHS 29-D. Color of the stripes: RHS 47-C and 5-D.

Rate of opening: Normal.

Sepals:

*Shape.*—Joined at lower part and sharp-pointed at extremity.
*Number.*—5 to 7.
*Color.*—Inside pea green: RHS 149B,145B. Outside lettuce green: RHS 144A,144C. Extremities approximate petal color.
*Striae.*—Longitudinal striae.

Calyx:
*Shape.*—Bell-shaped.
*Size.*—Large.
*Aspect.*—Smooth.
*Splitting.*—A little.

Peduncle:
*Length.*—About 68 cm.
*Character.*—Erect and rigid.
*Color.*—RHS 137A.

THE FLOWER

Blooming having: Recurrent and profuse.
Size of bloom: Very large.
*Diameter.*—About 9 cm.
*Depth.*—About 5.9 cm.
Borne: Singly.
Shape:
*When bloom first opens.*—High center.
*When bloom matures.*—Dome.
Petalage:
*Number of petals.*—110 (average).
*Number of florets.*—No.
Form: Fan shaped with very serrated apex.
Texture: Leathery.
Arrangement: Imbricated.
Appearance: Satiny.
Color:
*Outer petals.*—Body carrot red RHS 29A and 29B and stripes currant 47B, delft rose 47C and dresden yellow 5D, base greenish.
*Reverse side.*—Carrot red 29A and 29B and dresden yellow 5D, base greenish.
*Inside petals.*—Body carrot red RHS 29A and 29B and stripes currant 47B, delft rose 47C and dresden yellow 5D, base greenish.
*Reverse side.*—Carrot red 29A and 29B and dresden yellow 5A, base greenish.

Petaloids:
*Number.*—Between 4 to 9 depending on the flowers.
*Size.*—Smaller than petals.
*Color.*—Same as petals.
Discoloration after full bloom: A little.
Persistence: Greater than 20 days.
Lasting quality:
*As cut flower.*—About at least 10 days (in vase).
Disease resistant: Tolerance to *Fusarium oxysporum.*
Fragrance: Perceptible.

REPRODUCTIVE ORGANS

Stamens:
*Number.*—4 to 9.
*Arrangement.*—Around the ovary.
Anthers:
*Size.*—0.4 cm.
*Color.*—Yellowish.
Filaments:
*Length.*—1.1 cm.
*Color.*—Yellowish.
Pistils:
*Number.*—3 to 5.
Style:
*Length.*—2.3 cm.
*Color.*—Yellowish.
Stigmas: Yellowish.
Character of ovaries: Ribbed.
*Color.*—Greenish.

I claim:

1. A new and distinctive hybrid standard carnation plant, substantially as herein shown and described, characterized in particular by its recurrent profuse production of very large flowers, the serrated petals of which are in general of carrot red color and the body longitudinally brushed with current red, delft rose and dresden yellow with a greenish base, said plant having more than 120 leaves on a thick stem.

* * * * *

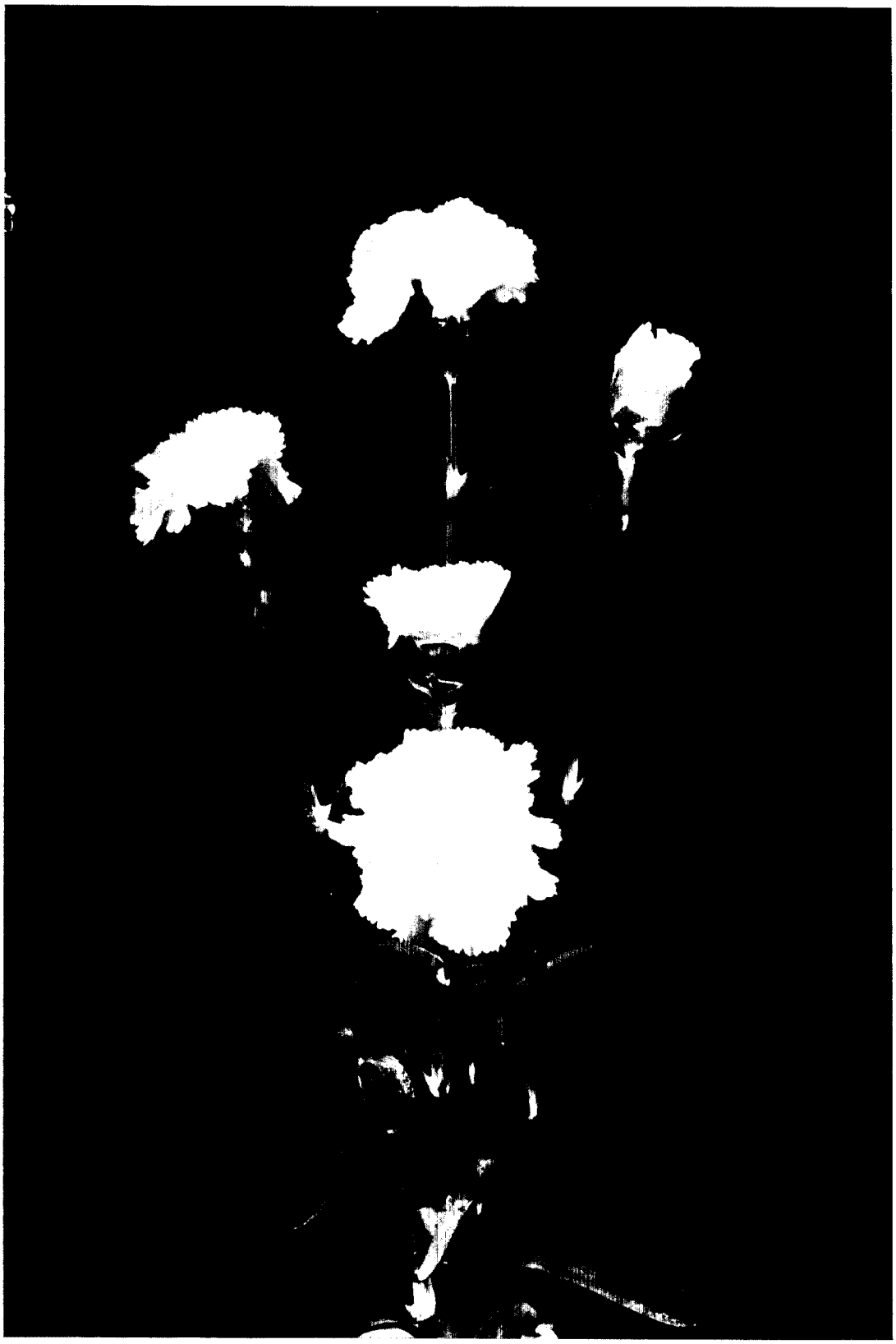

UNITED STATES PATENT AND TRADEMARK OFFICE

CERTIFICATE OF CORRECTION

PATENT NO. : PP 8,664

DATED : March 29, 1994

INVENTOR(S) : Jean-Louis Desclaux

It is certified that error appears in the above-indentified patent and that said Letters Patent is hereby corrected as shown below:

In column 1, line 2, delete "Le Pradet, France" and insert -- San Remo, Italy --;

In column 1, line 12, delete "San Remo, Italy" and insert -- Le Pradet, France --.

In column 2, line 2, delete "S112V" and insert -- S112U --;

In column 2, line 5, delete "S112V" and insert -- S112U --.

Column 4, line 2, delete "A: and insert --D--.

Signed and Sealed this

Twenty-ninth Day of November, 1994

*Attest:*

Bruce Lehman

BRUCE LEHMAN

*Attesting Officer*

*Commissioner of Patents and Trademarks*